United States Patent [19]

Myers, Jr. et al.

[11] 4,208,355

[45] Jun. 17, 1980

[54] DIMERIZATION OF NORBORNADIENE TO BINOR-S WITH A HOMOGENEOUS CATALYST

[75] Inventors: Harry K. Myers, Jr., Aston; Abraham Schneider, Overbrook Hills, both of Pa.

[73] Assignee: Suntech, Inc., St. Davids, Pa.

[21] Appl. No.: 714,204

[22] Filed: Aug. 13, 1976

[51] Int. Cl.$^2$ .............................................. C07C 3/21
[52] U.S. Cl. ...................................... 585/362; 60/208
[58] Field of Search ..................... 60/208; 260/666 PY

[56] References Cited

U.S. PATENT DOCUMENTS 3,113,424  12/1963  Wineman ................................ 60/208
3,147,589   9/1964  James ..................................... 60/208

*Primary Examiner*—Leland A. Sebastian
*Attorney, Agent, or Firm*—J. Edward Hess; Donald R. Johnson; Anthony Potts, Jr.

[57] ABSTRACT

Binor-S is prepared by the catalytic dimerization of norbornadiene (bicyclo[2.2.1]hepta-2,5-diene) using a homogeneous catalyst system of cobaltic acetylacetonate and diethylaluminum chloride and triphenyl phosphine. Ethylaluminum dichloride or aluminum ethylsesquichloride can be used in lieu of the diethylaluminum chloride. The reaction rate is rapid at an ambient temperature. Binor-S can be used as a precursor for hydrocarbons having utility as a high energy fuel.

12 Claims, No Drawings

DIMERIZATION OF NORBORNADIENE TO BINOR-S WITH A HOMOGENEOUS CATALYST

BACKGROUND OF THE INVENTION

The invention herein described was made in the course of or under a contract thereunder with the United States Air Force Systems Command.

This invention relates to the preparation of Binor-S. More particularly, the invention relates to the preparation of Binor-S. from norbornadiene. Still more particularly, the invention relates to the catalytic dimerization of norbornadiene to Binor-S using a three-component catalyst system.

Binor-S, upon further processing, can be converted into a component of a high energy fuel which can be used in either jet or rocket propulsion. Jet propulsion includes a jet engine which can be used for a missile plane and others and includes the three basic types, i.e., ramjet, turbo-jet and pulse jet. The term rocket generally refers to a device containing its own oxygen or oxidizing agent.

Binor-S is known by the systematic chemical name of endo-cis-endo-heptacy-clo(5.3.1.1$^{2,6}$.1$^{4,12}$.1$^{9,11}$.0$^{3,5}$.0$^{8,10}$)-tetradecane. Its melting point is about 65° C. It has a net volumetric heat of combustion of about 178,570 BTU/gallon.

Preparation of Binor-S is disclosed in an article in the Journal of the American Chemical Society, [88:21] Nov. 5, 1966, pages 4890–4894. The article is titled "π-Complex Multicenter Reactions Promoted by Binuclear Catalysts Systems. "Binor-S", a New Heptacyclotetradecane via Stereospecific Dimerization of Bicycloheptadiene", by G. N. Schrauzer, et al. Disclosed is the dimerization of bicycloheptadiene (also known as norbornadiene) to Binor-S using metal salts of cobalt carbonyl hydrides (e.g., Zn(Co(C0)$_4$)$_2$). A Lewis acid, such as AlBr$_3$, can be used as a cocatalyst with the transition metal carbonyl catalyst. Another related article appears in Tetrahedron Letters, No. 8, 1970, pages 543–545 titled "New Catalysts of Stereospecific Norbornadiene Dimerization to "Binor-S", by G. N. Schrauzer et al. This second article discloses the use of RhCl[P(C$_6$H$_5$)$_3$]$_3$ as a catalyst with BF$_3$0(C$_2$H$_5$)$_2$ as a cocatalyst for the dimerization of nobornadiene to Binor-S. The former two form a heterogenous catalyst system.

A metal-cobalt carbonyl complex useful as a catalyst in the polymerization of norbornadiene is disclosed in U.S. Pat. No. 3,679,722. Also, U.S. Pat. No. 3,676,474 discloses a multinuclear π-complex having at least two metal cobalt bonds which can be used as a catalyst in the dimerization of norbornadiene.

Catalytic dimerization of norbornadiene to Binor-S using a two component catalytic system of tris(triphenylphosphine) rhodium chloride and diethylaluminum chloride or ethylaluminum dichloride or aluminum ethylsesquichloride is disclosed in a related application, Ser. No. 631,978, filed Nov. 14, 1975, now U.S. Pat. No. 4,031,150.

Norbornadiene is also known as bicyclo(2.2.1)heptadiene-2,5. A method of preparation is disclosed in U.S. Pat. No. 2,875,256 issued February 24, 1959. Norbornadiene will be referred to as NBD hereinafter. NBD can be represented by either one of the following structural formulas:

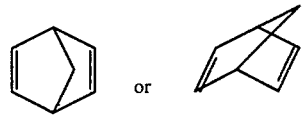

During the dimerization of NBD more than one dimer is possible. G. N. Schrauzer, in his review "On Transition Metal-Catalyzed Reaction of Norbornadiene and the Concept of a Complex Multicenter Processes" in Advances on Catalysis 18, 373 (1968) Acad. Press, describes the fourteen theoretically possible dimers of NBD. And any and each of the dimers described therein have different physical and chemical properties.

Thus, a specific synthesis problem in the dimerization of NBD, as can be visualized from the fourteen theoretically possible isomers, is to obtain both excellent selectivity and conversion to the desired isomer at as low an economic cost as possible.

SUMMARY OF THE INVENTION

NBD is rapidly dimerized to Binor-S at both excellent selectivity and conversion. The dimerization requires a catalytic amount of a three component catalytic system of cobaltic acetylacetonate, triphenyl phosphine and diethylaluminum chloride or ethylaluminum dichloride or aluminum sesquichloride. The components are referred to hereinafter as CoA$_3$, TPP, DEAC, EADC and EASC, respectively. The dimerization can occur at an ambient temperature.

The advantages of the present invention are as follows. Prior art methods are characterized by an extremely rapid exotherm, and to prevent runaway temperatures, high capacity heat exchange equipment is necessary. The investment cost and associated operating costs of this equipment adds substantially to the manufacturing cost of Binor-S. In contrast, present invention is not characterized by an extremely rapid exotherm and thus investment and operating cost savings are obtained.

Furthermore, the production of Binor-S from NBD is performed with both excellent selectivity and conversion. Furthermore, the reaction rate is rapid. Excellent selectivity and conversion, because the product is almost pure Binor-S, further facilitates the conversion of Binor-S to selectivity hydrogenated dimer mixtures having a ulitity as a high energy fuel. Since the product is mostly Binor-S the need to separate it from unreacted feed or other dimers or other compounds is minimized or obviated. Furthermore, the reaction occurs at a relatively low temperature and a relatively low pressure, both of which reduce relative manufacturing costs. By itself Binor-S also may have utility as a solid fuel.

DESCRIPTION

The catalytic dimerization of essentially NBD via present invention can be represented by the following formula reaction:

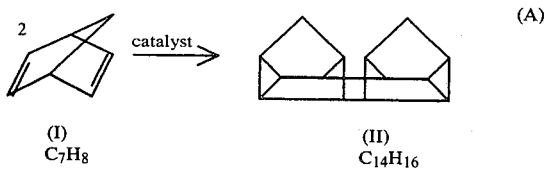

(A)

(I)
C₇H₈

(II)
C₁₄H₁₆ compound I is NBD while compound II is Binor-S which is also a C₁₄H₁₆ heptacyclic dimer of NBD. The structure of II is also often shown as follows:

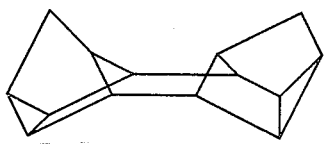

The NBD feed may contain a nominal amount of similar hydrocarbons; however, which if present should not be of a type which would adversely effect the reaction. If the NBD feed contains such undesirable hydrocarbons they can be removed by known means.

The Binor-S product can be separated from the other materials, that is unreacted NBD and the catalyst and other hydrocarbon. Also reaction A may also form nominal amounts of other dimers as well as heavier compounds. These heavier compounds as well as any unreacted feed and catalyst can be separated from the product by distillation, if necessary. An alternative procedure is that the catalyst can be deactivated by the addition of a hydroxylic solvent, e.g., methanol. This results in formation of two distinct layers which can be separated and then Binor-S can be distilled from other hydrocarbons, if necessary. Another separation procedure is crystallization from the quenched reaction product by cooling.

Generally the product from reaction A contains a major amount of Binor-S. Or expressed another way, a majority of the norbornadiene is dimerized to Binor-S. If the reaction is permitted to run for sufficient time then the product can contain substantial amounts of Binor-S. Based on the runs reported hereinafter the product can contain Binor-S in an excess of 90 mole %, however, a yield in excess of 80 mole % could also be economically acceptable. Again expressed another way the amount of norbornadiene dimerized to Binor-S can be in excess of at least 80 mole % and even in excess of 90 mole %. Such higher values are preferred.

The catalytic system favoring the aforementioned dimerization reaction A contains three components. The three are CoA₃, TPP and DEAC, EADC or AESC. The amount present is a catalytic amount so that a suitable conversion to Binor-S occurs and the selectivity as to Binor-S is sufficient. Material, which during the dimerization reaction could adversely effect the catalyst system, should not be present. For example, the presence of hydroxylic compounds such as water, alcohol or oxygen from air could deactivate the catalyst system.

Selectivity refers to the amount of particular compound formed divided by the amount of all compounds formed. Conversion to the dimer is the amount of total dimer formed divided by the sum of the total dimer plus unreacted feed. From a commercial standpoint economics of an overall process determines the optimal levels for both the selectivity and conversion.

The reaction time required for an economically satisfactory selectivity and/or conversion depend on a number of factors, such as catalyst to NBD ratio, as well as operating conditions. Also the economics depend on capital investment versus conversion per pass and the like. The catalyst to NBD ratios are discussed hereinafter while typical conditions are provided by the Examples.

An inert solvent can be used in the dimerization reaction. Since the reaction is mildly exothermic the solvent can serve as a heat sink. It can also assist in solubilizing the reaction components, that is the feed and the components of the catalyst and thereby provide for a homogeneous reaction medium. Some solvent can be added to the system as a carrier for one or more of the catalyst components. For example, DEAC is often maintained in a solvent such as toluene. Furthermore the solvent should not adversely react with the feed, products or catalyst, therefore it should be inert. Also, presence of the solvent can facilitate the handling of the reaction mixture. Classes of suitable inert solvents include aromatic hydrocarbons, cycloparaffins, cycloolefins, ethers, halogenated aromatics, halogenated paraffins and halogenated cycloparaffins. Specific examples include benzene, toluene, xylenes, cyclohexane, cyclopentadiene, diethylether, chlorobenzene, bromobenzene, chlorinated cyclohexane and the like. As to the amount of solvent used, excessive amounts decrease the reaction rate, and thus adversely affect the economics for a commercial operation. However, reaction A can take place without a solvent.

The dimerization of NBD with the three-component catalyst system can occur at ambient temperature. Thus the temperature of the homogeneous NBD-catalyst system mixture need not be raised to initiate reaction A. Of course, if the mixture is at an extremely low temperature, then heating of the cooled mixture could be necessary. However, once reaction A is underway, some heat is generated and the temperature of the mixture increases. If the temperature increases too much then some cooling would be required. Generally, however, the dimerization of NBD with the three-component catalyst system is not characterized by an extremely rapid exotherm.

Selective dimerization of the NBD occurs in a liquid phase therefore it is not desirable to have the reaction temperature largely exceed the boiling points of the NBD and/or solvent. Conversely, if the temperature is too low the reaction rate would be too low to be economically feasible. An operable temperature range is between from about 0° C. to about 150° C. with about 10° C. to about 100° C. a preferred range. The operating pressure can vary substantially, however, it can range from about atmospheric up to about 2000 psi with 1000 psi a preferred upper value. Process economics favor lower operating pressure, however, a moderately elevated reaction pressure may be desirable to keep gaseous reaction components, if any, in solution.

The amount of CoA₃ present compared to the NBD feed should be catalytically sufficient to obtain the desired product. Generally the mole ratio of NBD to CoA₃ can range between from about 50 to about 2000 with a preferred range between from about 100 to about 1000.

The second component of the catalyst system is TPP. The amount of this second component of the catalyst system should be catalytically sufficient to obtain the desired product. Generally the mole ratio of TPP to $CoA_3$ can range between from about 0.55 to about 100 with a preferred range between from about 1 to about 5.

DEAC, EADC, or EASC is the third component of the catalyst system with DEAC preferred. The amount of the third component can vary substantially but generally it relates to the amount of $CoA_3$ used. An effective mole ratio of DEAC, EADC or EASC to $CoA_3$ can be between from about 0.5 to about 100 with from about 1 to about 50 preferred and from about 3 to about 20 more preferred. Excess DEAC, EADC or EASC also serves as a scavenger for any water and/or oxygen in the system. Generally, however, when DEAC, EADC or EASC is used it is advantageous to conduct the reaction under substantially anhydrous conditions and under an inert gas blanket.

The feed to the process consists essentially of NBD. Other hydrocarbons, which could react with the NBD or with itself, should be avoided since such hydrocarbon could lower yields, and/or the effectiveness of the catalytic system.

The selective NBD dimerization of the present invention can be carried out in either a batch or a continuous process.

To further illustrate the invention, the following examples and comparisons are provided.

EXAMPLES

The accompanying Table summarizes the dimerization and comparative runs which were carried out in 15 milliliter pyrex vessels closed with wired serum caps fitted with an internal immersion thermometer. The procedure was as follows. In comparative run 1 the $CoA_3$, TPP and NBD were added to the vessel. The resulting mixtures was deaerated by flushing with argon. After the deaeration the mixture was cooled from a temperature of about 24° C. to −60° C. The cooling was for safety reasons; initially it was thought that the resulting exotherm would be extremely rapid. Then DEAC, in a 1 molar solution with toluene, was added. The DEAC solution was at room temperature so the temperature of the resulting mixture increased above the aforementioned −60° C. The resulting mixture was warmed to room temperature and then the temperature of the combination of DEAC, NBD, TPP and $CoA_3$ gradually increased by itself and reached a maximum of 55° C. During the warming the color of the mixture of $CoA_3$, TPP and NBD changed from an initial green solution to brown with the assimilation of DEAC and gradually then changed to amber. And then during the final warming period, a precipitate formed. As shown in the Table, little or no conversion occurred after 74 minutes.

Run 2 was essentially a repeat of Run 1 except that the amount of TPP used was increased. As shown in the Table, after 42 minutes the conversion was 29% and the selectivity as to Binor-S was in excess of 90%.

Run 3 also was essentially a repeat of Run 1 except that the amount of TPP used was increased compared to Runs 1 or 2. As shown in the Table both the conversion and selectivity were excellent.

Run 4 was different (from Runs 1–3) in that an ether ($CH_3CH_2O-CH_2CH_3$) was used as a solvent and that the mixture of $CoA_3$, TPP, NBD and the ether was cooled from about 24° C. to 0° C. Then the DEAC was added and the mixture warmed. As shown in the Table both the conversion and selectivity were in excess of 95%.

Run 5 was different from the previous runs in that the mixture of $CoA_3$, TPP and NBD, after deaeration of 24° C., was warmed to 65° C. to insure that all the components were in solution. Afterwards, the mixture was cooled to −20° C. After cooling, the DEAC was added. However, upon adding the DEAC, a rapid exotherm and evolution of gas (about 5 minutes) caused the resulting mixture to boil. For safety reasons after 22 minutes the reaction vessel was quenched in a −65° C. bath. The conversion was 73.4% whereas the selectivity was 95.3%.

While in Run 5 the initial color of the solution was green, as in all runs, it turned yellow with the addition of the DEAC and then turned to a hazy amber.

Run 6 was made using cyclopentadiene as a solvent. The $CoA_3$, TPP and NBD were mixed, deaerated, and then warmed to 60° C. to insure that all the components were in solution. Then the mixture was cooled to −29° C. At the lower temperature the DEAC was added, and the mixture was warmed. The cyclopentadiene was then added and again the mixture was warmed. The addition of the latter caused an orange colored precipitate. As shown in the Table, after 90 minutes the conversion was 32% and the selectivity was 73%, excluding the precipitate.

Comparisons of Runs 1 and b 2 indicate that a catalytic amount of the three component system need be present to obtain Binor-S. Comparison of Runs 2 and 3 indicate that the use of additional TPP increases the conversion and reaction rate. Runs 4 and 6 indicate that solvents can be used.

Analogous results will be obtained when other solvents, e.g., benzene, toluene, xylene, cyclohexane, chlorobenzene, bromobenzene, chlorinated cyclohexane are used and/or EADC or EASC is used in lieu of DEAC.

TABLE

DIMERIZATION OF NBD TO FORM BINOR-S

| Run | NBD | Amounts of[5] $CoA_3$[2] | TPP[2] | DEAC[7] | Time[3] (minutes) | Maxmum Temp. °C. | Additional Solvent[6] (Amount) | % NBD Conversion[1] | % Binor-S Selectivity[1] |
|---|---|---|---|---|---|---|---|---|---|
| 1 | 1 ml | 7.5 mg | 3 mg[4] | 0.4 ml | 74 | 55 | none | nil | n.a. |
| 2 | 1 ml | 7.5 mg | 7 mg | " | 42 | 55 | none | 29 | 90 |
| 3 | 1 ml | 7.5 mg | 20 mg | " | 10 | 55[9] | none | 96 | 90 |
| 4 | 0.9 ml | 7 mg | 4 mg | " | overnight | 50 | ether (0.9 ml) | 95 | 95 |
| 5 | 1 ml | 7 mg | 21 mg | 8 | 22 | 92 | none | 73.4 | 95.3 |
| 6 | 1 ml | 7 mg | 14 mg | 0.4 ml | 90 | 80 | cyclopentadiene | 32 | 73 |

| | | Amounts of[5] | | | Time[3] | Maxmum | Additional Solvent[6] | % NBD | % Binor-S |
|---|---|---|---|---|---|---|---|---|---|
| Run | NBD | CoA₃[2] | TPP[2] | DEAC[7] | (minutes) | Temp. °C. | (Amount) | Conversion[1] | Selectivity[1] |
| | | | | | | | (0.4 ml) | | |

TABLE-continued

DIMERIZATION OF NBD TO FORM BINOR-S

[1] Based on analysis via gas chromatography.
[2] The weights shown are approximate.
[3] Time is from addition of DEAC to the sample.
[4] TPP/CoA₃ mole ratio = .543.
[5] ml = milliliters, mg = milligrams.
[6] Other than toluene.
[7] One molar in toluene.
[8] 10 weight % DEAC in toluene.
[9] Exotherm to 92° C. may have occurred.

The invention claimed is:

1. Process for the catalytic dimerization of norbornadiene comprising:
reacting a feed consisting essentially of norbornadiene in the presence of a catalytic amount of a three-component catalytic system of cobaltic acetylacetonate and triphenyl phosphine and diethylaluminum chloride or ethylaluminum chloride or aluminum ethylsesquichloride and at a temperature between from about 0° C. to about 150° C. thereby dimerizing a majority of the norbornadiene to Binor-S.

2. Process according to claim 1 wherein the Binor-S is separated from the other materials.

3. Process according to claim 1 wherein an inert solvent is present.

4. Process according to claim 2 wherein the amount of norbornadiene dimerized to Binor-S is in excess of 80 mole %.

5. Process according to claim 1 wherein the mole ratio of norbornadiene to cobaltic acetylacetonate ranges from between about 50 to about 2000.

6. Process according to claim 5 wherein the mole ratio of the triphenylphosphine to the cobaltic acetylacetonate ranges from between about 0.55 to about 100.

7. Process according to claim 6 wherein the mole ratio of diethylaluminum chloride, ethylaluminum dichloride or aluminum ethylsesquichloride to cobaltic acetylacetonate ranges from between about 0.5 to 100.

8. Process according to claim 7 wherein the temperature ranges between from about 10° C. to about 100° C.

9. Process according to claim 8 wherein the Binor-S is separated from the other materials.

10. Process according to claim 9 wherein the amount of norbornadiene dimerized to Binor-S is in excess of 80 mole %.

11. Process according to claim 10 wherein the amount or norbornadiene dimerized to Binor-S is in excess of 90 mole %.

12. Process according to claim 11 wherein an inert solvent is present and is selected from the group consisting of aromatic hydrocarbons, cycloparaffins, cycloolefins, ethers, halogenated aromatics, halogenated paraffins and halogenated cycloparaffins.

* * * * *